(12) United States Patent
Urasaki (10) Patent No.: US 7,811,227 B2
(45) Date of Patent: Oct. 12, 2010

(54) ENDOSCOPE APPARATUS AND COMMUNICATION METHOD USED IN THE APPARATUS

(75) Inventor: Takeshi Urasaki, Tachikawa (JP)

(73) Assignee: Olympus Medical Systems Corp., Tokyo (JP)

( * ) Notice: Subject to any disclaimer, the term of this patent is extended or adjusted under 35 U.S.C. 154(b) by 1085 days.

(21) Appl. No.: 11/508,450

(22) Filed: Aug. 23, 2006

(65) Prior Publication Data
US 2007/0049798 A1   Mar. 1, 2007

(30) Foreign Application Priority Data
Aug. 24, 2005 (JP) .............................. 2005-243284

(51) Int. Cl.
*A61B 1/00* (2006.01)
(52) U.S. Cl. ........................................ 600/118; 600/101
(58) Field of Classification Search ................. 600/101, 600/103, 117, 118, 109; 709/228, 233
See application file for complete search history.

(56) References Cited

U.S. PATENT DOCUMENTS

| | | | | |
|---|---|---|---|---|
| 5,163,161 | A * | 11/1992 | Bowles et al. ............. | 455/164.1 |
| 7,161,907 | B2 * | 1/2007 | Mott ........................... | 370/232 |
| 7,562,152 | B2 * | 7/2009 | Moore et al. ................ | 709/233 |
| 2003/0063188 | A1 | 4/2003 | Takahashi et al. | |
| 2005/0070761 | A1 * | 3/2005 | Higuchi ....................... | 600/109 |
| 2005/0210144 | A1 * | 9/2005 | Kumagai et al. ............ | 709/229 |
| 2005/0215857 | A1 * | 9/2005 | Iwasaki ....................... | 600/118 |
| 2005/0278463 | A1 * | 12/2005 | Ando ........................... | 710/8 |
| 2006/0155166 | A1 * | 7/2006 | Takahashi et al. ........... | 600/109 |
| 2008/0125135 | A1 * | 5/2008 | Uchida et al. ............ | 455/452.1 |

FOREIGN PATENT DOCUMENTS

| | | |
|---|---|---|
| EP | 1 347 638 A1 | 9/2003 |
| JP | 08-6099 | 1/1996 |
| JP | 11-177654 | 7/1999 |
| JP | 2000-79094 | 3/2000 |
| JP | 2001-017390 | 1/2001 |
| JP | 2003-265410 | 9/2003 |
| JP | 2005-006856 | 1/2005 |
| JP | 2005-153288 | 6/2005 |

* cited by examiner

*Primary Examiner*—John P Leubecker
(74) *Attorney, Agent, or Firm*—Scully, Scott, Murphy & Presser, P.C.

(57) ABSTRACT

An endoscope apparatus includes an endoscope, a signal processing unit, and a communication unit. The endoscope includes an information storage section including an endoscope information memory and a first controller controlling readout of the information in the endoscope information memory. The endoscope is detachably connected to the signal processing unit, which includes a second controller issuing at least an instruction for a readout operation of the information to the information storage section. Data is transmitted and received between the first controller and the second controller through the communication unit. The endoscope apparatus includes a communication speed setting unit setting the communication speed of the communication unit to a higher communication speed allowable in the first controller and a switching unit switching the communication speed.

17 Claims, 7 Drawing Sheets

ENDOSCOPE APPARATUS AND COMMUNICATION METHOD USED IN THE APPARATUS

This application claims benefit of Japanese Patent Application No. 2005-243284 filed in Japan on Aug. 24, 2005, the contents of which are incorporated by this reference.

BACKGROUND OF THE INVENTION

1. Field of the Invention

The present invention relates to an endoscope apparatus that includes an endoscope and a signal processing unit and performs endoscopy and to a communication method in the endoscope apparatus.

2. Description of the Related Art

Endoscopes are in widespread use in medical and industrial fields in recent years. Endoscopes provided with image pickup devices are used with being connected to signal processing apparatuses performing signal processing for the image pickup devices.

For example, an endoscope apparatus disclosed in Japanese Unexamined Patent Application Publication No. 2003-265410 has information storing means including a non-volatile memory and a central processing unit (CPU) functioning as control means in a connector unit of the electronic endoscope. A white balance setting etc. are stored in the non-volatile memory.

In this endoscope apparatus, data communication between the CPU in the electronic endoscope and a processor functioning as a signal processing apparatus has a fixed communication speed.

The communication speed in the data communication between the electronic endoscope and the processor depends on the performance of the respective CPUs in the processor and the information storing means and the stability of the system.

SUMMARY OF THE INVENTION

According to an embodiment of the present invention, there is provided an endoscope apparatus including an endoscope, a signal processing unit, and a communication unit. The endoscope includes an information storage section including an endoscope information memory in which information concerning the endoscope is stored and a first controller controlling readout of the information stored in the endoscope information memory. The endoscope is detachably connected to the signal processing unit, which includes a second controller issuing at least an instruction for a readout operation of the information to the information storage section. Data is transmitted and received between the first controller and the second controller through the communication unit. The endoscope apparatus includes a communication speed setting unit setting the communication speed of the communication unit to a higher communication speed allowable in the first controller; and a switching unit switching the communication speed on the basis of the result produced in the communication speed setting unit.

According to the present invention, there is provided a communication method in an endoscope apparatus including an endoscope and a signal processing unit. The endoscope includes an information storage section including an endoscope information memory in which information concerning the endoscope is stored and a first controller controlling readout of the information stored in the endoscope information memory. The endoscope is detachably connected to the signal processing unit, which includes a second controller issuing at least an instruction for a readout operation of the information to the information storage section. Data is transmitted and received between the first controller and the second controller through a communication unit. The communication method includes the steps of setting the communication speed of the communication unit to a higher communication speed allowable in the first controller; and switching the communication speed on the basis of the setting result in the step of setting the communication speed.

DESCRIPTION OF THE PREFERRED EMBODIMENTS

Embodiments of the present invention will be described with reference to the attached drawings.

First Embodiment

Figure 1:
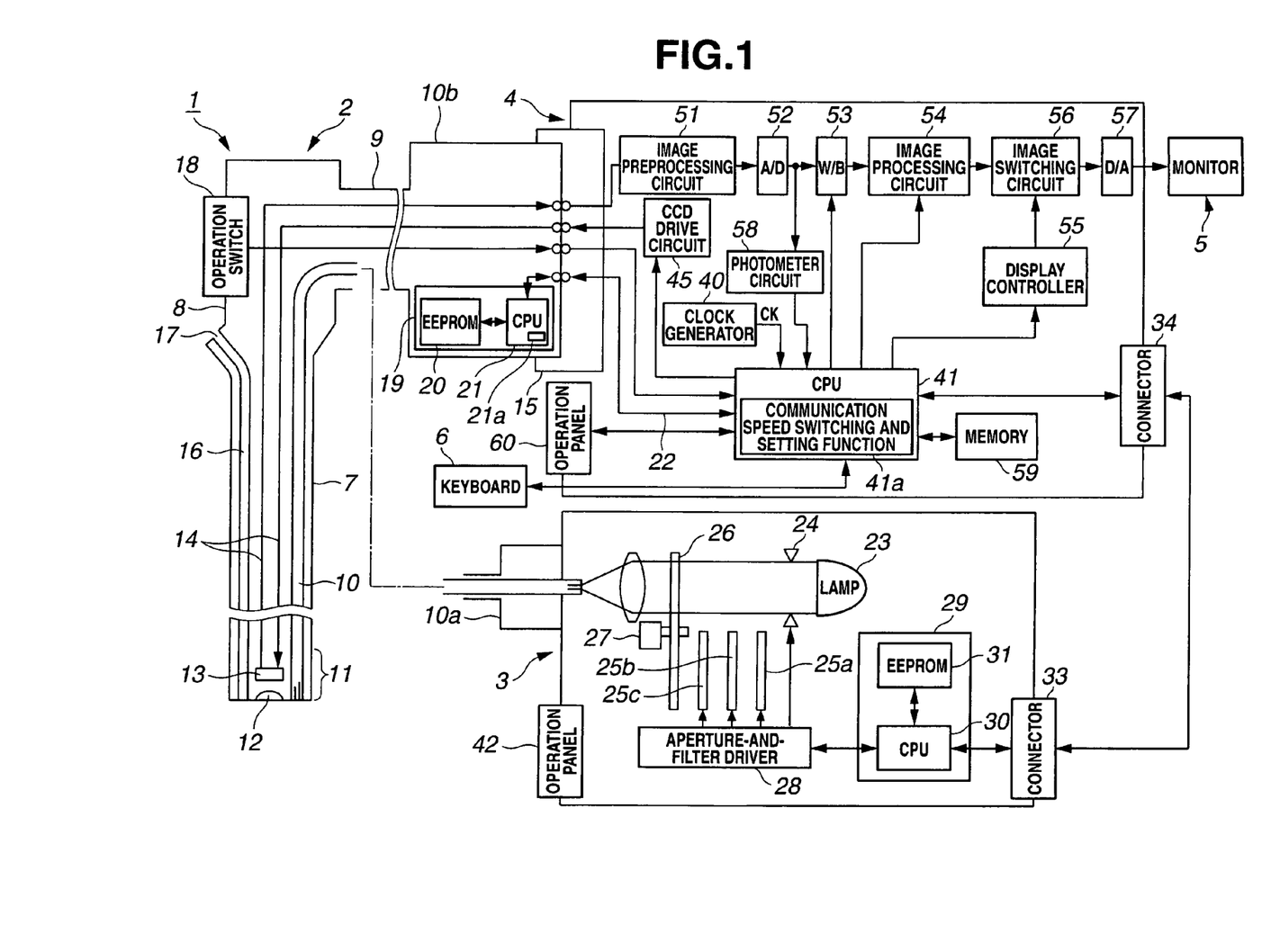
FIG. 1 is a block diagram showing an entire structure of an endoscope apparatus according to a first embodiment of the present invention.
Figure 2:
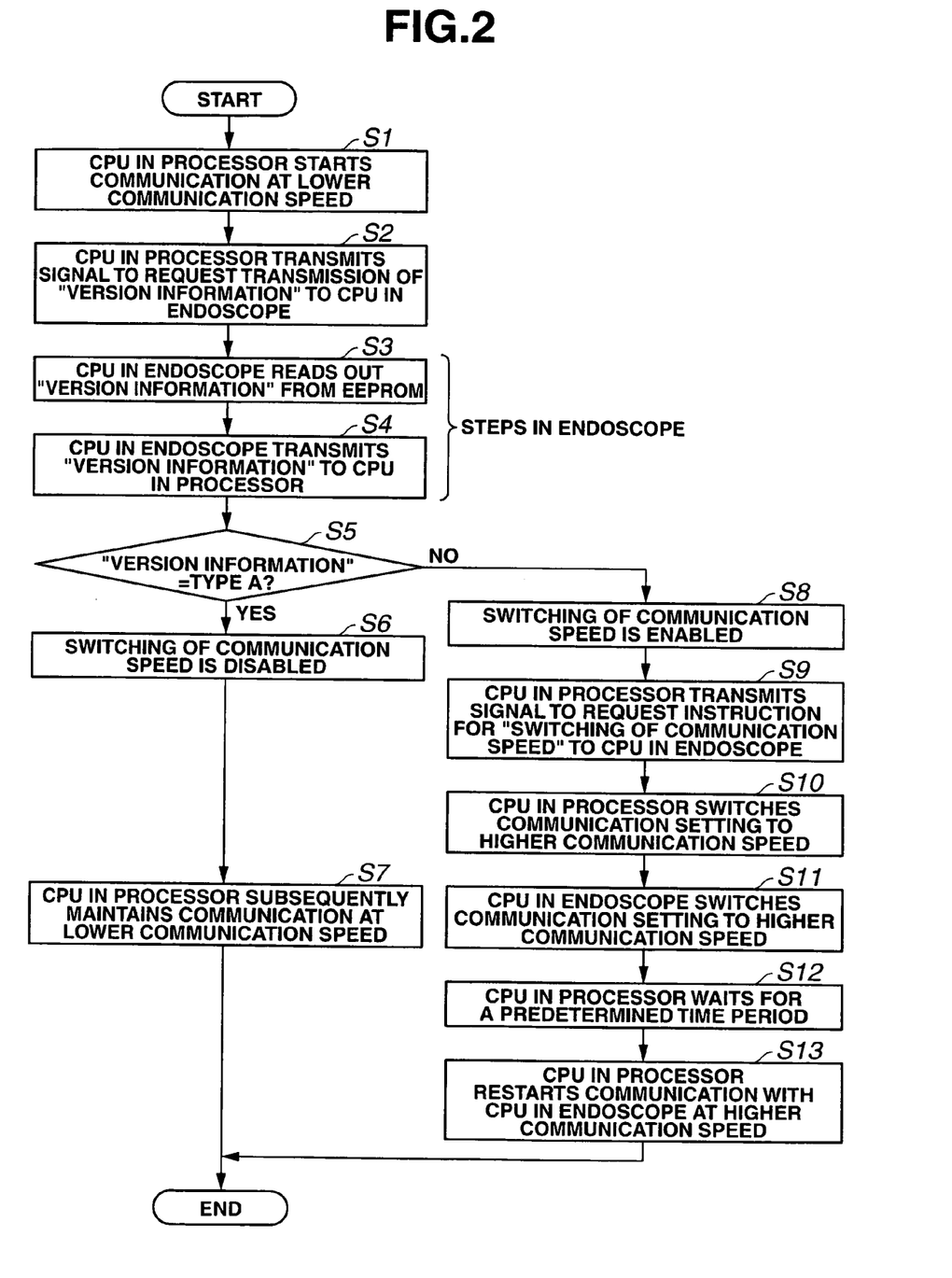
FIG. 2 is a flowchart showing an operation of the endoscope apparatus according to the first embodiment of the present invention.

FIG. 1 is a block diagram showing an entire structure of an endoscope apparatus according to a first embodiment of the present invention. FIG. 2 is a flowchart showing an operation of the endoscope apparatus according to the first embodiment of the present invention.

Referring to FIG. 1, an endoscope apparatus 1 according to the first embodiment of the present invention includes an electronic endoscope (hereinafter referred to as an endoscope) 2, a light source unit 3, a processor 4, a monitor 5, and a keyboard 6. The endoscope 2 is inserted into a body cavity to observe and treat a subject, such as an affected part of the body. The light source unit 3 transmits RGB light for normal observation and special light for special observation to the endoscope 2. The processor 4 functions as a signal processing unit and performs signal processing to an image capturing signal captured by the endoscope 2 to generate a video signal. The monitor 5 receives the video signal from the processor 4 to display an endoscopic image corresponding to the video signal. The keyboard 6 is connected to the processor 4 and allows input of information concerning the patient and various commands.

The endoscope 2 includes an insertion section 7 inserted into the body cavity of the patient and an operating section 8 provided at the rear end of the insertion section 7. A universal cable 9 extends from the operating section 8.

A light guide 10 through which illumination light is transmitted is inserted through the insertion section 7. A light guide connector 10a at the rear end of the light guide 10 is detachably connected to the light source unit 3. The illumination light (narrowband illumination light in a special light mode or excitation light in a fluorescent mode) which is emitted from the light source unit 3 and is transmitted through the light guide 10 goes out from the distal end face of the light guide 10 mounted to an illumination window of the distal end 11 of the insertion section 7. The subject, such as the effected area, is irradiated with the illumination light.

An observation window (image-capturing window) is provided adjacent to this illumination window. An objective lens system 12 is mounted to the observation window. For example, a charge coupled device (abbreviated to CCD) 13, functioning as a solid-state image pickup device, is arranged at the image forming location of the objective lens system 12.

Signal lines 14 connected to the CCD 13 extend through the insertion section 7, the operating section 8, and the universal cable 9. The trailing ends of the signal lines 14 reach a signal connector 10b. The signal connector 10b is detachably connected to a signal connector retainer 15 of the processor 4.

An endo-therapy (ET) product channel 16 is provided in the insertion section 7. The ET product channel 16 has an opening 17 for an ET product near the front end of the operating section 8. The ET product is inserted from the opening 17. The ET product channel 16 has a tip opening at the tip of the distal end 11. The tip of the ET product through the ET product channel 16 protrudes from the tip opening to perform a treatment, for example, to sample affected tissue or to resect a diseased part with the ET product.

Operation switches 18 including an observation-mode selection switch allowing switching between observation modes, and etc, are provided in, for example, the operating section 8 in the endoscope 2. The operation switches 18 are connected to the contacts of the signal connector 10b through signal lines. When the signal connector 10b is connected to the signal connector retainer 15, the operation switches 18 are connected to a CPU 41, functioning as control means, in the processor 4.

An endoscope information storage section 19 is provided, for example, in the signal connector 10b in the endoscope 2. The endoscope information storage section 19 has a variety of information specific to the endoscope 2 stored therein. The endoscope information storage section 19 functions as a CCD storage section in which information concerning the endoscope 2, more specifically, CCD information about the number of pixels, etc. of the CCD 13 mounted to the endoscope 2 is stored.

The endoscope information storage section 19 includes an electronically erasable and programmable read only memory (EEPROM) 20 and a CPU 21. The EEPROM 20, which is an electronically rewritable non-volatile memory, has a variety of information concerning the endoscope 2 stored therein. The CPU 21 functions as control means for writing (storing) information in the EEPROM 20 and reading out the information stored in the EEPROM 20.

The EEPROM 20 has a) information concerning a higher communication speed allowable in the CPU 21, specifically, version information about the CPU 21, stored therein. Depending on the type or performance of the CPU 21, either of two kinds of version information, for example, Type A and Type B, is stored in the EEPROM 20 as the maximum or higher communication speed allowable in the communication (hereinafter simply referred to as the allowable communication speed or the communication speed for simplicity, except for confusing cases).

In this case, if the CPU 21 supports only lower communication speed (for example, 1,200 bits per second (bps)), the version information about Type A is stored in EEPROM 20 as information concerning the allowable communication speed. If the CPU 21 supports higher communication speed (for example, 9,600 bps), the version information about Type B is stored in the EEPROM 20.

The EEPROM 20 further has b) the model name of the endoscope, c) data on the number of pixels of the image pickup device in the endoscope, d) information concerning the ET product channel in the endoscope (the inside diameter of the ET product channel, direction and position with respect to the image pickup scope of the image pickup device, and information concerning an applicable ET product), e) white balance setting value, and so on stored therein.

The CPU 21 is connected to the CPU 41, functioning as control means, in the processor 4 via a communication line 22 with the signal connector 10b being connected to the signal connector retainer 15. When power is applied, communication is established between the CPU 41 in the processor 4 and the CPU 21 in the endoscope 2 via the communication line 22, functioning as a communication unit, to transmit and receive information.

According to the first embodiment of the present invention, a single line, other than a grounded line, is used as the communication line 22 to transmit and receive the information.

The light source unit 3 includes a lamp 23 emitting the illumination light including visible light.

The illumination light emitted from the lamp 23 is incident on band-limiting filters 25a to 25c for the special light and an RGB rotating filter 26 after the amount of the illumination light that is transmitted is adjusted by an aperture 24 arranged in the optical path. The light transmitted through the RGB rotating filter 26 is condensed by a condenser lens and is incident on the incident end of the light guide 10.

The RGB rotating filter 26 is rotated by a motor 27.

The aperture 24 and the band-limiting filters 25a to 25c are driven by an aperture-and-filter driver 28. The aperture ratio of the aperture 24 is adjusted by the aperture-and-filter driver 28. The band-limiting filters 25a to 25c are arranged on the optical path of the illumination light or are evacuated therefrom depending on a selected observation mode of the special light. The drive operation of the aperture-and-filter driver 28 is controlled via a light source controller 29, functioning as light source control means, in the light source unit 3.

When only the RGB rotating filter 26 is arranged in the optical path, as in the case shown in FIG. 1, the RGB illumination light corresponding to the normal observation mode is supplied to the light guide 10. In contrast, if the band-limiting filters 25a to 25c are inserted into the optical path, the special light corresponding to, for example, an infrared light, the narrowband light, the excitation light in the fluorescent mode is supplied to the light guide 10.

The light source controller 29 includes a CPU 30 and an EEPROM 31. The CPU 30 functions as control means for controlling the components in the light source unit 3. The EEPROM 31 functions as a non-volatile memory and has information specific to the light source unit 3 stored therein. Writing (storing) of information in the EEPROM 31 and readout of the stored information from the EEPROM 31 are controlled by the CPU 30.

The EEPROM 31 has, for example, the following data stored therein: 1) model name of the light source unit, 2) identification information of the special light filter mounted in the light source unit, 3) data about usage of the light source unit (the number of times the light source unit is used, the operating time of the light source unit, the total time when the lamp is turned on, the total number of times the RGB rotating filter and the band-limiting filters are used, and the total operating time thereof).

The CPU 30 is connected to a connector 34 in the processor 4 via a connector 33 in the light source unit 3 and a signal line for communication. The CPU 30 is capable of two-way communication with the CPU 41, functioning as control means, in the processor 4.

The light source unit 3 also includes an operation panel 42. The operation panel 42 is provided with multiple operation switches with which an observation-mode switching operation for switching the illumination light used for observation (also called an observation light) and other operations are performed.

For example, in response to the observation-mode switching operation, the operation signal is supplied to the CPU 30 that performs a control operation corresponding to the operation signal and transmits the operation signal to the CPU 41 in the processor 4. The CPU 41 controls the processor 4 so as to perform signal processing corresponding to the switched observation mode.

When the observation mode switch in the operation switches 18 in the operating section 8 of the endoscope 2 is operated, the CPU 41 in the processor 4 performs the control operation corresponding to the operation in the processor 4. The CPU 41 transmits the operation signal to the CPU 30 in the light source unit 3 to control the CPU 30 so as to supply the illumination light corresponding to the observation mode to the light guide 10 of the endoscope 2.

The internal structure of the processor 4 will now be described. A CCD drive circuit 45 that applies a CCD drive signal to the CCD 13 to drive the CCD 13 is provided in the processor 4. The CPU 41 supplies a control signal corresponding to the CCD 13 mounted in the endoscope 2 connected to the processor 4 to the CCD drive circuit 45 that generates the CCD drive signal corresponding to the CCD 13 even with a different number of pixels being used.

The CCD 13 outputs a signal subjected to photoelectric conversion in response to the applied CCD drive signal. This signal is supplied to an image preprocessing circuit 51 in the processor 4. The image preprocessing circuit 51 performs correlated double sampling (CDS) and so on.

The output signal from the image preprocessing circuit 51 is supplied to an analog-to-digital (A/D) conversion circuit 52 (abbreviated to "A/D" in FIG. 1) converting the analog signal into a digital signal. The digital video signal subjected to the A/D conversion in the A/D conversion circuit 52 is supplied to a white balance circuit 53 (abbreviated to "W/B" in FIG. 1) performing white balance processing. The output signal from the white balance circuit 53 is supplied to an image processing circuit 54 performing image processing, for example, structural enhancement and color enhancement.

The output signal from the image processing circuit 54 is supplied to an image switching circuit 56 that performs switching between this output signal and a video signal corresponding to a menu screen or setup screen generated by a display controller 55 or combines this output signal with the video signal to output the switched or combined signal. The output signal from the image switching circuit 56 is supplied to a digital-to-analog (D/A) conversion circuit 57 (abbreviated to "D/A" in FIG. 1) where the signal is converted into an analog video signal that is supplied to the monitor 5.

The output signal from the A/D conversion circuit 52 is also supplied to a photometer circuit 58 that measures the brightness of the image in order to automatically control the amount of the illumination light. The photometer circuit 58 performs photometry. Photometric modes include peak measurement for detecting a peak of the brightness of the image, average measurement for detecting an average brightness of the image, and automatic measurement for detecting the brightness near the center of the image.

The photometer circuit 58 or the CPU 41 to which the measured signal is supplied compares the measured signal with a reference value of the brightness to be set and generates a light control signal so as to reduce the difference between the measured signal and the reference value. The generated light control signal is supplied to the CPU 30 in the light source unit 3 through the connectors 34 and 33. The CPU 30 adjusts the aperture ratio of the aperture 24 via the aperture-and-filter driver 28 and performs automatic light control so as to provide an appropriate brightness corresponding to the reference value.

The processor 4 includes a memory 59, such as a non-volatile memory, storing a variety of information. The CPU 41 performs a control operation, described below, in accordance with information of a control program stored in the memory 59.

An operation panel 60 is provided on the front face of the processor 4. With the operation panel 60 and the keyboard 6, it is possible to perform various operations instructing, for example, switching between the observation modes and setting of the white balance to the CPU 41.

The CPU 41 controls the white balance circuit 53, the display controller 55, etc., in addition to the image processing circuit 54.

Information, such as the white balance setting, depending on the characteristics of the CCD 13 of the endoscope 2 connected to the processor 4 can be written from the CPU 41 to the EEPROM 20 through the CPU 21.

In this case, the CPU 41 transmits a command to write information in the EEPROM 20 to the CPU 21. The CPU 21 stores the information in the EEPROM 20 in response to the command.

When the same endoscope 2 is connected to the processor 4, the CPU 41 reads out the information stored in the EEPROM 20 to, for example, set the white balance and the like in a shorter time, compared with the case where the white balance is set without using the information.

The endoscope apparatus 1 having the structure described above is characterized in that the version information is stored in the EEPROM 20 in the endoscope information storage section 19 provided in the signal connector 10b of the endoscope 2 as the information concerning the communication speed (the higher communication speed allowable in the data communication) of the CPU 21.

The CPU 41 in the processor 4 transmits a signal (instruction signal) to request transmission of the version information concerning the communication speed to the CPU 21 when the endoscope 2 is connected to the processor 4. In other words, the CPU 41 in the processor 4 instructs the CPU 21 to read out the version information as the information concerning the communication speed, stored in the EEPROM 20.

The CPU 21 reads out the version information from the EEPROM 20 in response to the instruction signal and transmits the readout version information to the CPU 41.

The CPU 41 in the processor 4 has a communication speed switching and setting function 41a that uses the transmitted version information to switch the communication speed to the communication speed supported by the CPU 21 in the endoscope 2 and set the communication speed supported by the CPU 21 in the endoscope 2. The CPU 41 in the processor 4 is characterized by using the communication speed switching and setting function 41a to perform the communication at the communication speed appropriate for the CPU 21 in the endoscope 2 connected to the processor 4.

The communication speed switching and setting function 41a includes a communication speed setting function and a communication speed switching function. The communication speed setting function divides a clock CK generated by a clock generator 40 with a frequency divider circuit (not shown) to generate a clock having a predetermined communication speed. Information is transmitted and received in synchronization with the generated clock.

The communication speed switching function is used to switch the division ratio of the frequency divider circuit, thereby switching the communication speed.

The CPU 41 is set so as to perform the communication at a lower communication speed before the CPU 41 obtains the version information and the communication speed is switched on the basis of the version information.

However, in initial products, the communication speed cannot possibly be switched to a higher communication speed because the lower communication speed is the maximum communication speed.

At startup, the CPU 21 in the endoscope 2 is also set so as to have the communication speed equal to the lower communication speed set in the CPU 41 at startup. The CPU 21 also has a communication speed switching and setting function 21a used for switching the communication speed. The communication speed switching and setting function 21a includes a communication speed setting function and a communication speed switching function. The communication speed setting function and the communication speed switching function may be realized in the same manner as in the processor 4. Or, the communication speed setting function may be realized by a phase locked loop (PLL) circuit.

The CPU 21 in the endoscope 2 also has a control function to write a variety of information concerning the endoscope 2 in the EEPROM 20 included in the endoscope 2.

Information can be written in the EEPROM 20 in response to a writing instruction issued from the CPU 41. In this case, information to be stored and the writing instruction are input with, for example, the keyboard 6. The CPU 41 issues the writing instruction into the EEPROM 20 in response to the input operation to write the information to be stored in the EEPROM 20 through the CPU 21.

An operation of the endoscope apparatus 1, according to the first embodiment of the present invention, will be described with reference to the flowchart in FIG. 2. The processor 4 and the light source unit 3 are activated by connecting the signal connector 10b of the endoscope 2 to the processor 4 and connecting the light guide connector 10a to the light source unit 3 to turn on the power. Then, the CPU 41 in the processor 4 reads out the program stored in the memory 59 to be activated. The CPU 21 in the endoscope 2 is also activated. In this state, in Step S1 in FIG. 2, the CPU 41 starts communication at a lower communication speed (the lower communication speed of Type A and Type B, that is, the communication speed corresponding to Type A).

In Step S2, the CPU 41 in the processor 4 transmits a signal to request transmission of information concerning the communication speed allowable in the CPU 21, that is, the "version information" to the CPU 21 in the endoscope 2.

Upon reception of the transmission request signal, in Step S3, the CPU 21 in the endoscope 2 reads out the "version information" from the EEPROM 20. In Step S4, the CPU 21 in the endoscope 2 transmits the readout "version information" to the CPU 41 in the processor 4.

Upon reception of the "version information", in Step S5, the CPU 41 in the processor 4 determines whether the "version information" is Type A.

If the CPU 41 in the processor 4 determines that the "version information" is Type A, then in Step S6, the CPU 41 in the processor 4 determines that the switching of the communication speed is disabled. In Step S7, the CPU 41 in the processor 4 subsequently maintains the communication at the lower communication speed.

If the CPU 41 in the processor 4 determines in Step S5 that the "version information" is not Type A, then in Step S8, the CPU 41 in the processor 4 determines that the switching of the communication speed is enabled.

In Step S9, the CPU 41 in the processor 4 transmits a signal to request instruction for the "switching of the communication speed" to the CPU 21 in the endoscope 2.

In Step S10, the CPU 41 in the processor 4 switches the communication speed setting to a higher communication speed.

Upon reception of the signal to request an instruction for the "switching of the communication speed" in Step S9, in Step S11, the CPU 21 in the endoscope 2 switches the communication speed setting to the higher communication speed.

After transmitting the signal to request an instruction for the "switching of the communication speed" in Step S9, then in Step S12, the CPU 41 in the processor 4 waits for a predetermined time period during which the CPU 21 in the endoscope 2 receives the instruction request signal and switches the communication speed setting to the higher communication speed in accordance with the instruction request signal.

After the predetermined time period elapses, in Step S13, the CPU 41 in the processor 4 restarts the communication with the CPU 21 in the endoscope 2 at the higher communication speed. Specifically, the CPU 41 in the processor 4 transmits a signal to request transmission of information including b) the model name of the endoscope, c) data on the number of pixels of the image pickup device in the endoscope, d) information concerning the ET product channel in the endoscope (the inside diameter of the ET product channel, direction and position with respect to the image pickup scope of the image pickup device, and information concerning an applicable ET product), and e) white balance setting value and etc, described above.

After receiving the above information from the CPU 21 in the endoscope 2, the CPU 41 in the processor 4 temporarily stores the information in the memory 59. In this case, it is possible to reduce the communication time in which the information is transmitted from the CPU 21 in the endoscope 2 to the CPU 41 in the processor 4 if the higher communication speed is set.

The CPU 41 in the processor 4 supplies a control signal to the CCD drive circuit 45 in accordance with the information stored in the memory 59 to cause the CCD drive circuit 45 to generate the CCD drive signal corresponding to the CCD 13 mounted to the endoscope 2 connected to the processor 4.

If the information concerning the white balance setting value is supplied, the CPU 41 performs the white balance control to the white balance circuit 53 by the use of the information concerning the white balance setting value. The CPU 41 displays information concerning the ET product channel 16 of the endoscope 2 in, for example, the monitor 5.

The processor 4 can perform the drive operation and signal processing appropriate for the CCD 13 by using the information read out from the endoscope 2 even if the CCD 13 of a different model is mounted to the endoscope 2.

In the above operation according to the first embodiment of the present invention, the CPU 41 in the processor 4 can surely obtain the "version information" about the (higher) communication speed of the CPU 21 in the endoscope information storage section 19 provided in the endoscope 2 connected to the processor 4 with the communication speed setting being set to the lower communication speed.

As a result, the CPU 41 switches the communication speed setting to the higher communication speed depending on whether the CPU 21 supports the higher communication speed.

Accordingly, if the CPU 21 supports the higher communication speed, it is possible to perform the communication at the higher communication speed and, therefore, to reduce the communication time required for, for example, reading out information from the EEPROM 20.

According to the first embodiment of the present invention, it is also possible to decrease the number of communication lines in the endoscope 2 (it is sufficient to use one communication line 22, in addition to the ground line) and to decrease the number of contacts of the signal connector 10b (it is sufficient for the signal connector 10b to have one contact).

A modification of the first embodiment will now be described. Although the version information is stored in the EEPROM 20 in the first embodiment, communication speed information indicating the value of the communication speed is stored in the EEPROM 20 in this modification.

Specifically, the EEPROM 20 stores communication speed information Ca, Cb, and Cc (Ca<Cb<Cc), such as 1200 bps, 4800 bps, and 9600 bps, supported by the CPU 21 in the endoscope 2.

According to this modification, the CPU 21 in the endoscope 2 initially starts communication with the CPU 41 in the processor 4 at a lowest communication speed (for example, Ca=1200 bps), and the CPU 41 reads out the communication speed information via the CPU 21.

If the readout communication speed information indicates that no communication speed information exist or indicates the lowest communication speed as at the start of the communication, the CPU 41 keeps the lowest communication speed. In contrast, if the readout communication speed information indicates a communication speed higher than the communication speed at the start of the communication, the CPU 41 transmits a command to switch the communication speed to a communication speed on the basis of the communication speed information to the CPU 21 in the endoscope 2.

Upon reception of the command, the CPU 21 in the endoscope 2 switches the communication speed setting to the instructed speed. The CPU 41 in the processor 4 switches the communication speed setting to the instructed speed after transmitting the command and performs the communication at the switched higher communication speed after a predetermined time period.

At this time, the CPU 21 in the endoscope 2 may return a reception response of the command to the CPU 41 in the processor 4 so that the CPU 41 can surely confirm that the CPU 21 has received the command. The CPU 41 in the processor 4 may wait for the response and switch the communication speed in response to the reception response.

Figure 3:
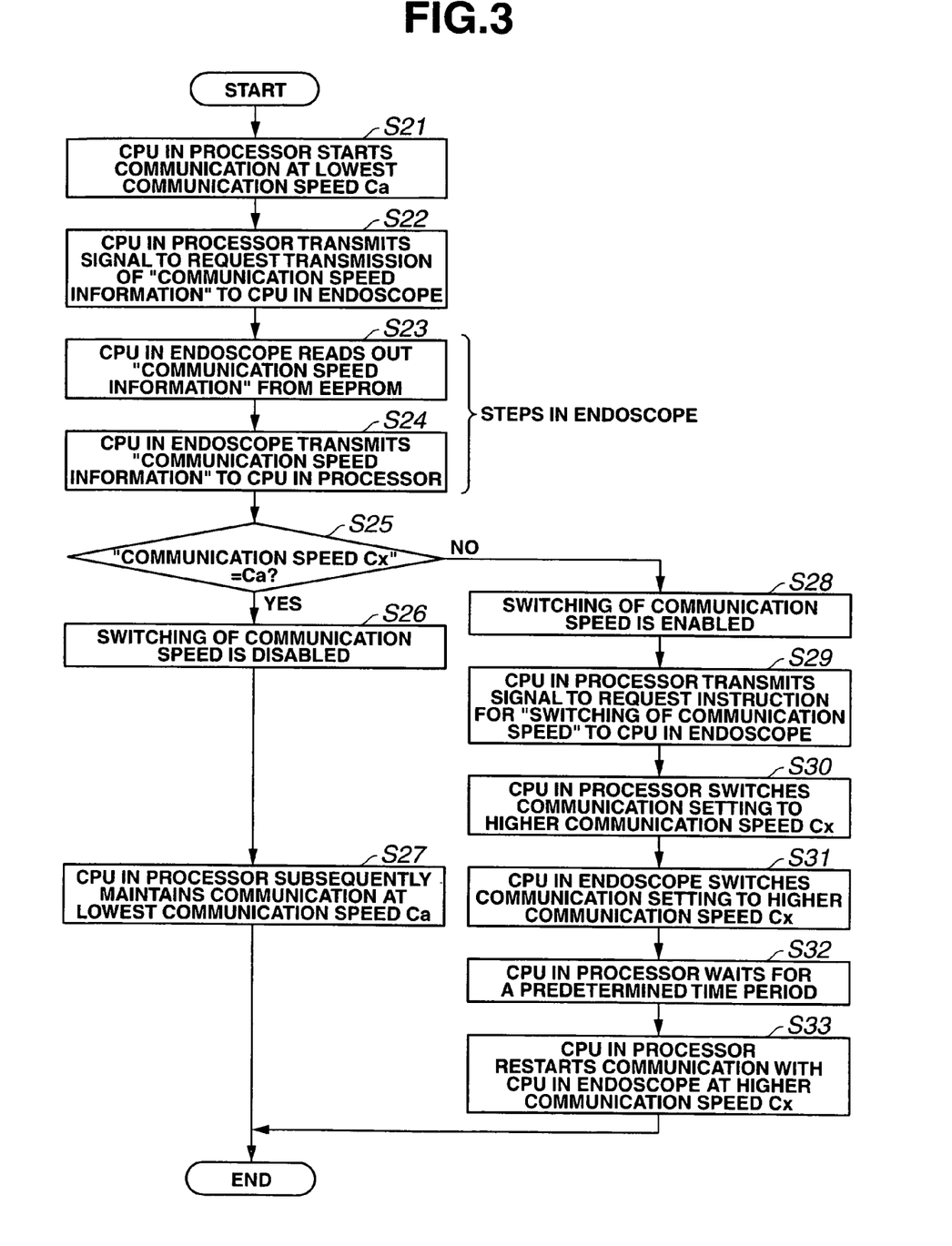
FIG. 3 is a flowchart showing an operation according to a modification of the first embodiment of the present invention.

FIG. 3 is a flowchart showing an operation according to this modification. Steps S21 to S24 in FIG. 3, according to this modification, are almost the same as Steps S1 to S4 in FIG. 2, except that the "version information" is replaced with the "communication speed information". However, since the above three communication speeds Ca, Cb, and Cc can be used in this modification, the description in the steps in FIG. 3 is slightly different from that in FIG. 2.

Referring to FIG. 3, in Step S21, the CPU 41 starts communication at a lowest communication speed Ca. In Step S22, the CPU 41 in the processor 4 transmits a signal to request transmission of the "communication speed information" to the CPU 21 in the endoscope 2.

Upon reception of the transmission request signal, in Step S23, the CPU 21 in the endoscope 2 reads out the "communication speed information" from the EEPROM 20.

In the next Step S24, the CPU 21 in the endoscope 2 transmits the readout "communication speed information" to the CPU 41 in the processor 4. In the next Step S25, the CPU 41 in the processor 4 determines whether the communication speed Cx in the transmitted "communication speed information" coincides with the lowest communication speed Ca (Cx=Ca).

If the CPU 41 in the processor 4 determines that the communication speed Cx coincides with the lowest communication speed Ca (including the case where information concerning the communication speed is not stored), then in Step S26, the CPU 41 in the processor 4 determines that the switching of the communication speed is disabled. In Step S27, the CPU 41 in the processor 4 subsequently maintains the communication at the lowest communication speed Ca.

If the CPU 41 in the processor 4 determines in Step S25 that the communication speed Cx does not coincide with the lowest communication speed Ca, then in Step S28, the CPU 41 in the processor 4 determines that the switching of the communication speed is enabled.

In Step S29, the CPU 41 in the processor 4 transmits a signal to request an instruction for the "switching of the communication speed" to the CPU 21 in the endoscope 2. In Step S30, the CPU 41 in the processor 4 switches the communication speed setting to the communication speed Cx higher than the communication speed Ca.

Upon reception of the signal to request an instruction for the "switching of the communication speed" from the CPU 41 in the processor 4, in Step S31, the CPU 21 in the endoscope 2 switches the communication speed setting to the communication speed Cx higher than the communication speed Ca.

In Step S32, the CPU 41 in the processor 4 waits for a predetermined time period. Thereafter in Step S33, the CPU 41 in the processor 4 restarts the communication with the CPU 21 in the endoscope 2 at the higher communication speed Cx.

According to this modification of the first embodiment of the present invention, since the communication can be established at the communication speed allowable in the CPU 21 in the endoscope 2, it is possible to transmit the information in a short time, as in the first embodiment. Accordingly, the user can perform the endoscopy with a short delay. In addition, it is possible to improve the operability of the endoscope apparatus.

Although the communication between the CPU 21 in the endoscope 2 and the CPU 41 in the processor 4 is described above, the CPU 41 in the processor 4 may transmit the information to the CPU 30 in the light source unit 3 or the CPU 30 in the light source unit 3 may transmit the information to the CPU 41 in the processor 4.

In other words, the communication speed of the communication between the CPU 41 in the processor 4 and the CPU 30 in the light source unit 3 may be set to a communication speed allowable in the CPU 30 in the light source unit 3.

Second Embodiment

Figure 4:
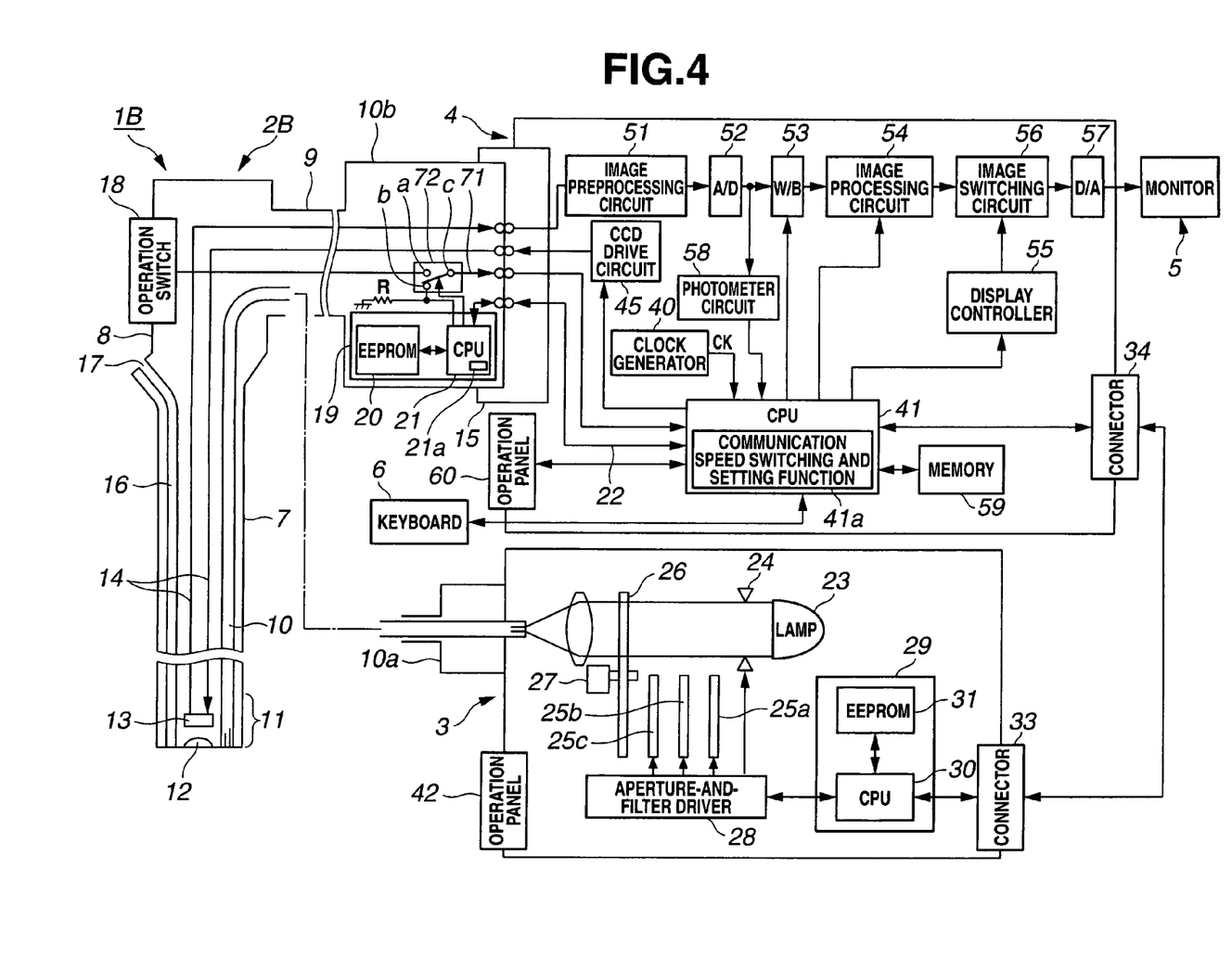
FIG. 4 is a block diagram showing an entire structure of an endoscope apparatus according to a second embodiment of the present invention.

Second embodiment of the present invention will be described with reference to FIGS. 4 and 5. FIG. 4 is a block diagram showing a structure of an endoscope apparatus 1B according to the second embodiment of the present invention.

Modifying part of the endoscope 2 in the endoscope apparatus 1 shown in FIG. 1 provides an endoscope 2B employed in the endoscope apparatus 1B.

The endoscope 2B includes a switch 72 along a signal line 71 extending from the contact of the signal connector 10b to the operation switches 18. A control signal supplied from the CPU 21 controls the switch 72. In this case, a common contact c of the switch 72 is connected to the contact of the signal connector 10b, one change-over contact a thereof is connected to the operation switches 18, and the other change-over contact b is connected to the CPU 21.

At power-on (when power is applied from the processor 4 to the CPU 21), the switch 72 is set such that the common contact c is connected to the change-over contact b, as shown in FIG. 4. When the communication between the CPU 21 and the CPU 41 in the processor 4 is established in the state in FIG. 4, the signal line 71 is used as transmitting means through which information is transmitted, in addition to the communication line 22 shared between the transmission and the reception.

The change-over contact b is grounded, for example, via a pull-down resistor R. In order to establish the communication with the CPU 41 in the processor 4 after the power is applied, the CPU 21 controls the voltage level of the signal line 71 to, for example, perform one-way transmission of information to the CPU 41.

After the signal line 71 is used in the communication for reading out the information, that is, after the readout of the information from the EEPROM 20 is terminated, the CPU 41 in the processor 4 transmits a signal indicating that the readout of the information is terminated to the CPU 21 in the endoscope 2.

Upon reception of this signal, the CPU 21 controls switching of the contacts of the switch 72. Specifically, the CPU 21 controls the switch 72 such that the common contact c is connected to the change-over contact a. The signal line 71 subsequently functions as transmitting means through which a signal from the operation switches 18 is transmitted.

The other components in the endoscope apparatus 1B are the same as those in the endoscope apparatus 1 according to the first embodiment of the present invention.

Figure 5:
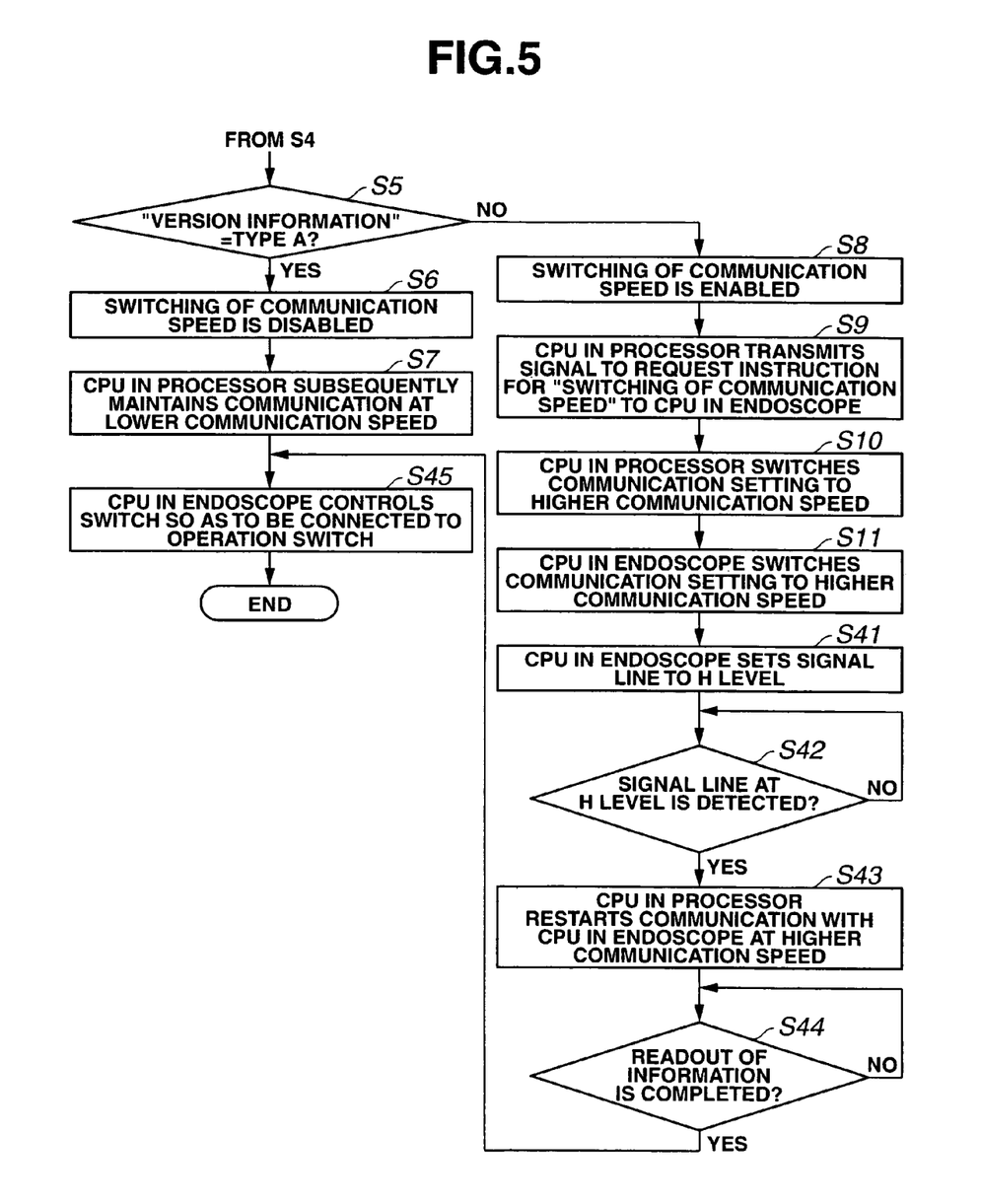
FIG. 5 is a flowchart showing part of an operation of the endoscope apparatus, according to the second embodiment of the present invention.

Next, an operation of the present embodiment is described referring to FIG. 5. FIG. 5 is a flowchart showing part of an operation of the endoscope apparatus 1B, according to the second embodiment of the present invention. Since the operation shown in FIG. 5 is similar to that in FIG. 2 according to the first embodiment of the present invention, only the steps different from those in FIG. 2 will be described.

At power-on, the CPU 41 in the processor 4 and the CPU 21 in the endoscope 2 are activated and the common contact c is connected to the change-over contact b in the switch 72.

Steps S1 to S5 described above with reference to FIG. 2 are performed (Steps S1 to S4 are omitted in FIG. 5). If the CPU 41 in the processor 4 determines in Step S5 that the "version information" is Type A, Steps S6 and S7 are performed, as in FIG. 2, and the operation proceeds to Step S45.

If the CPU 41 in the processor 4 determines in Step S5 that the "version information" is not Type A, Steps S8 to S11 are performed, as in FIG. 2. After switching the communication speed setting to the higher communication speed in Step S11, then in Step S41, the CPU 21 in the endoscope 2 changes the voltage level of the signal line 71 from "LOW" to "HIGH" (abbreviated to "H" in FIG. 5) so that the processor 4 can detect that the setting of the communication speed is terminated.

In Step S42, the CPU 41 in the processor 4 waits for detection of the "HIGH" voltage level in the signal line 71. If the "HIGH" voltage level in the signal line 71 is detected, in Step S43, the CPU 41 in the processor 4 restarts the communication with the CPU 21 in the endoscope 2 at the higher communication speed.

The CPU 21 in the endoscope 2 transmits the information stored in the EEPROM 20 to the CPU 41 in the processor 4. In Step S44, the CPU 21 in the endoscope 2 waits for termination of the readout of the information stored in the EEPROM 20 by the CPU 41 in the processor 4.

When the readout of the information is terminated, in Step S45, the CPU 21 in the endoscope 2 controls the switch 72 so that the common contact c is connected to the change-over contact a, which is connected to the operation switches 18. In this state, an operation, such as selection of an observation mode, can subsequently be performed with the operation switches 18.

According to the second embodiment of the present invention, in addition to the communication line 22 used in both the transmission and the reception, the signal line 71 is used for the one-way transmission of the signal. Accordingly, it is possible to reduce the waiting time and to surely transmit the response signal, compared with the case where only the communication line 22 is used in both the transmission and the reception.

Consequently, more efficient communication can be achieved with higher reliability in the second embodiment, compared with the first embodiment. In other words, the CPU 41 in the processor 4 can read out the information stored in the endoscope 2 in a time period shorter than that in the first embodiment.

Figure 6:
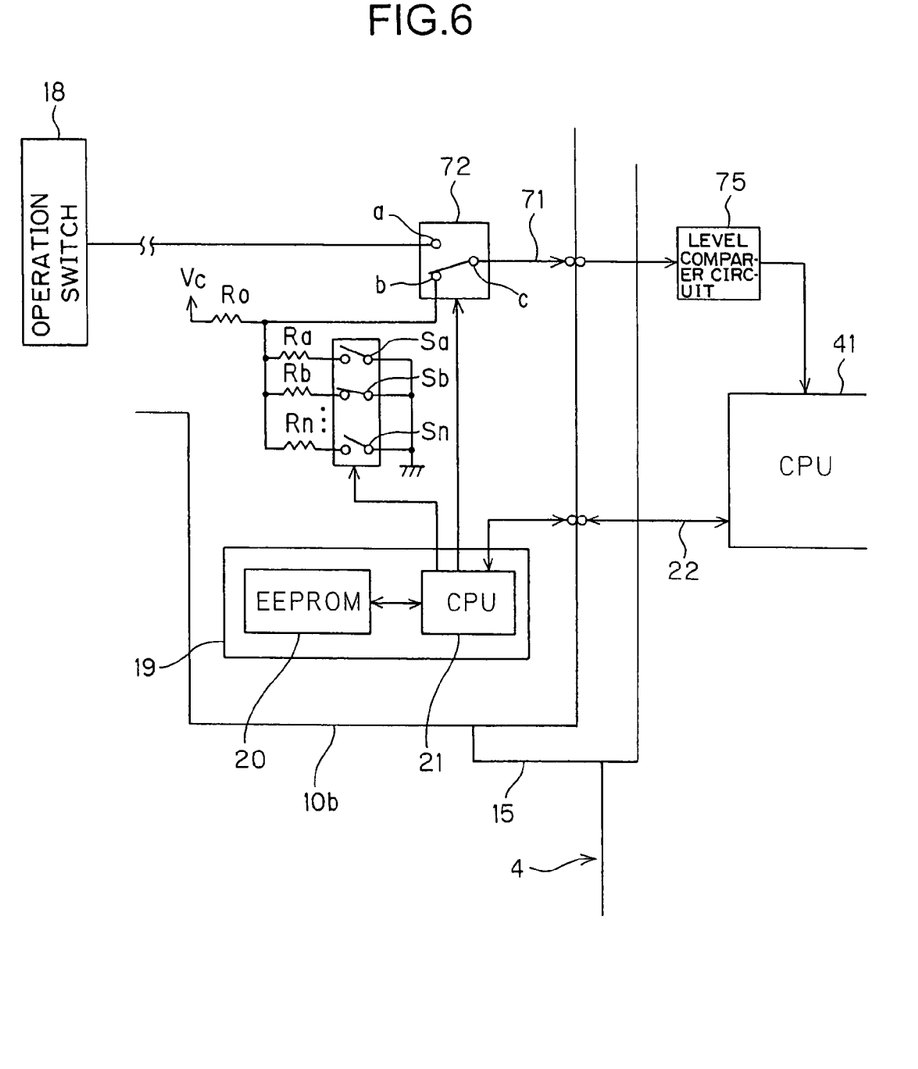
FIG. 6 is a block diagram showing a structure near the signal connector in an endoscope apparatus according to a modification of the second embodiment of the present invention.

FIG. 6 is a block diagram showing a partial structure near the signal connector 10b in an endoscope apparatus according to a modification of the second embodiment of the present invention. According to this modification, at startup, information concerning the communication speed of the CPU 21 in an endoscope 2B is transmitted to the CPU 41 in the processor 4 through the signal line 71.

The structure according to the modification of the second embodiment differs from that in FIG. 4 according to the second embodiment in part of the structure of the signal connector 10b.

According to this modification, the change-over contact b of the switch 72 in FIG. 4 is connected to a power terminal Vc via a reference resistor Ro and is also connected to one end of multiple resistors Ra, Rb, . . . , Rn. The multiple resistors Ra, Rb, . . . , Rn have different resistances and the other end of the multiple resistors Ra, Rb, . . . , Rn is grounded via switches Sa, Sb, . . . , Sn connected in series to the multiple resistors Ra, Rb, . . . , Rn.

One of the switches Sa, Sb, . . . , Sn is selectively turned on by the CPU 21.

The multiple resistors Ra, Rb, . . . , Rn are provided in order to support multiple communication speeds.

When power is applied to the CPU 21 to be activated, the CPU 21 reads out program information stored in the EEPROM 20. The CPU 21 selectively turns on a switch Si connected in series to a resistor Ri (i=a, b, . . . , n) corresponding to a communication speed in accordance with the readout information concerning the communication speed of the CPU 21, stored in the EEPROM 20.

In other words, the CPU 21 turns on the switch Si connected to the resistor Ri corresponding to the communication speed of the CPU 21 as the operation in the initial power-on state.

In this case, the voltage level of the signal line 71 is given by dividing the voltage of the power terminal Vc by the resistances of the resistors Ri and Ro.

According to this modification of the second embodiment, the CPU 41 obtains the level of the signal input through the signal line 71 through a level comparer circuit 75. The level comparer circuit 75 determines in a binary level whether an operation, such as an instruction for switching between the observation modes, is performed with the operation switches 18. The level comparer circuit 75 also determines the voltage level given by connecting the common contact c to the change-over contact b and dividing the voltage by the resistance of the resistor Ri and outputs the determined voltage level to the CPU 41.

When power is applied to the CPU 41 in the processor 4 to be activated, the CPU 41 obtains information about the voltage detected by the level comparer circuit 75 through the signal line 71 and detects information about the communication speed of the CPU 21 in the endoscope 2 connected to the processor 4 on the basis of the obtained information about the voltage.

The CPU 41 in the processor 4 requests switching and setting of the communication speed so as to establish the communication with the CPU 21 in the endoscope 2 at the detected communication speed and, then, starts the communication at the detected communication speed.

Alternatively, the CPU 41 in the processor 4 may immediately establish the communication with the CPU 21 in the endoscope 2 at the detected communication speed without requesting the switching and setting of the communication speed. In this case, the CPU 21 in the endoscope 2 selectively turns on the switch Si connected in series to the resistor Ri (i=a, b, . . . , n) corresponding to the communication speed of the CPU 21 at the power-on and sets the communication speed. Then, the CPU 21 in the endoscope 2 waits for communication with the CPU 41 in the processor 4.

The communication between the CPU 41 in the processor 4 and the CPU 21 in the endoscope 2 can be established in the manner described above.

Figure 7:
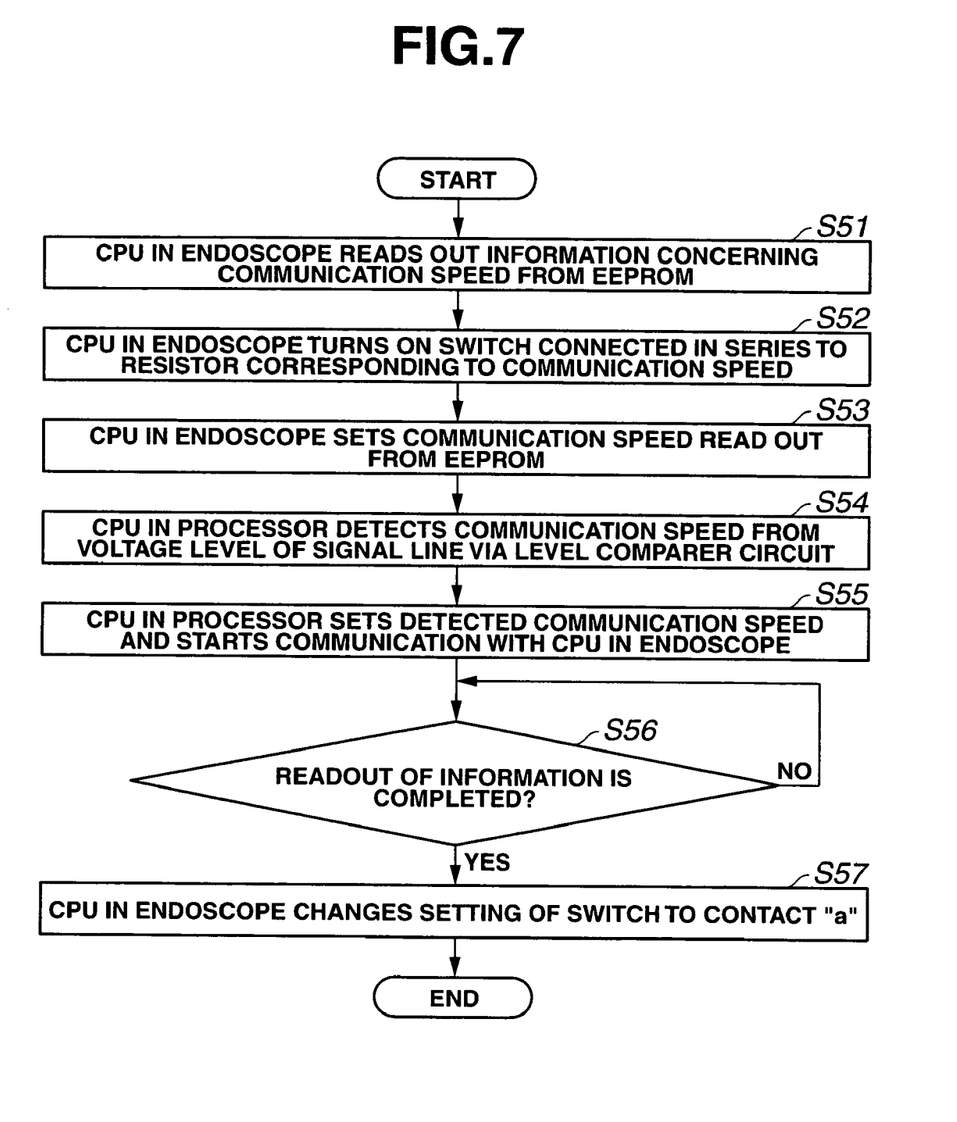
FIG. 7 is a flowchart showing an operation of the endoscope apparatus according to the modification of the second embodiment of the present invention.

FIG. 7 is a flowchart showing an operation of the endoscope apparatus according to the modification of the second embodiment of the present invention.

When power is applied to the CPU 21 in the endoscope 2B to be activated, in Step S51, the CPU 21 in the endoscope 2B reads out program information stored in the EEPROM 20. The CPU 21 then reads out information about the communication speed of the CPU 21, stored in the EEPROM 20.

In Step S52, the CPU 21 selectively turns on the switch Si connected in series to the resistor Ri (i=a, b, . . . , n) corresponding to the communication speed.

As a result, the voltage level of the signal line 71 is set to a value corresponding to the communication speed of the CPU 21.

In Step S53, the CPU 21 in the endoscope 2 sets the communication speed to be used to the communication speed read out from the EEPROM 20. Specifically, the CPU 21 sets the communication speed used in the communication with the CPU 41 in the processor 4 to the maximum communication speed allowable in the CPU 21.

In Step S54, the CPU 41 in the processor 4 detects information about the communication speed of the CPU 21 from the voltage level of the signal line 71 via the level comparer circuit 75 connected to the signal line 71.

In Step S55, the CPU 41 in the processor 4 sets the communication speed used in the communication to the detected communication speed and, then, starts the communication with the CPU 21 via the communication line 22 at the set communication speed.

The CPU 41 establishes the communication with the CPU 21 to read out information necessary for the processor 4.

In Step S56, the CPU 21 in the endoscope 2 waits for an indication that the readout of the information from the CPU 41 is terminated.

After receiving the indication that the readout of the information is terminated, in Step S57, the CPU 21 in the endoscope 2 controls the switch 72 such that the common contact c is connected to the change-over contact a. The signal line 71 is subsequently used for the operation of transmitting the operation signal from the operation switches 18 to the CPU 41.

According to this modification of the second embodiment of the present invention, when power is applied to the endoscope 2, the CPU 21 in the endoscope 2 immediately transmits information about the voltage level corresponding to the communication speed allowable in the CPU 21 to the processor 4 through the signal line 71, different from the communication line 22.

Accordingly, the CPU 41 in the processor 4 can rapidly set the (higher) communication speed allowable in the CPU 21, without transmitting a request to transmit information about the communication speed to the CPU 21 in the endoscope 2.

Consequently, it is possible to reduce the time required for the communication between the CPU 41 in the processor 4 and the CPU 21 in the endoscope 2. In addition, since the signal line 71, different from the communication line 22, is used to transmit the information about the communication speed (specifically, the voltage level), stable communication can be achieved.

Also in the first embodiment and so on, the CPU 21 in the endoscope 2 may transmit the information about the communication speed of the CPU 21 to the CPU 41 in the processor 4, without a signal to request transmission of the information about the (higher) communication speed transmitted from the CPU 41 in the processor 4 to the CPU 21 in the endoscope 2 at the startup.

In the embodiments and modifications described above, it is assumed that the higher communication speed of the CPU 41 is higher than the higher communication speed of the CPU 21 when the communication between the CPU 21 in the endoscope 2 (2B) and the CPU 41 in the processor 4 is established.

If the higher communication speed of the CPU 21 is higher than the higher communication speed of the CPU 41, the CPU 41 may switch the communication speed to the higher communication speed of the CPU 41 and may also switch the communication speed of the CPU 21 to the higher communication speed of the CPU 41.

The following operation is performed, for example, in the modification of the first embodiment of the present invention by adapting the above method. The higher communication speed of the CPU 41 is denoted by Cy, which is higher than the lowest communication speed Ca.

In FIG. 3 showing the operation according to the modification of the first embodiment, Steps S21 to S28 are performed in the manner described above. If the CPU 41 in the processor 4 determines in Step S25 that the communication speed Cx is higher than the lowest communication speed Ca, then in Step S28, the CPU 41 in the processor 4 determines that the switching of the communication speed is enabled.

Before proceeding to Step S29, the CPU 41 performs the following determination process. The CPU 41 compares the communication speed Cx with the communication speed Cy to determine a communication speed Cz, which is the lower one of the communication speed Cx and the communication speed Cy.

In the steps subsequent to Step S29 in FIG. 3, the operation is performed with the communication speed Cx being replaced with the communication speed Cz. In other words, the communication speed to be used is switched and set to the communication speed Cz allowable in both the CPU 21 and the CPU 41 to establish the communication.

The case where the higher communication speed Cx of the CPU 21 is higher than the higher communication speed Cy of the CPU 41 can be accommodated in the manner described above.

Having described the preferred embodiment and modification of the invention referring to the accompanying drawings, it should be understood that the present invention is not limited to the precise embodiment and modification and various changes and modifications thereof could be made by one skilled in the art without departing from the spirit and scope of the invention as defined in the appended claims.

What is claimed is:

1. An endoscope apparatus comprising:
an endoscope that includes an information storage section including an endoscope information memory in which information concerning the endoscope is stored and a first controller controlling readout of the information stored in the endoscope information memory;
a signal processing unit to which the endoscope is detachably connected and which includes a second controller issuing at least an instruction for a readout operation of the information to the information storage section;
a communication unit through which data is transmitted and received between the first controller and the second controller;
a communication speed setting unit setting the communication speed of the communication unit to a higher communication speed allowable in the first controller; and
a switching unit switching the communication speed on the basis of a result produced in the communication speed setting unit,
wherein the second controller transmits to the first controller a command to switch the communication speed to the higher communication speed and to set the higher communication speed on the basis of information concerning the higher communication speed allowable in the first controller, the information being stored in the endoscope information memory.

2. The endoscope apparatus according to claim 1, wherein the first controller controls writing and readout of the information in and from the endoscope information memory, and the second controller issues an instruction for writing and readout operations of the information to the information storage section.

3. The endoscope apparatus according to claim 2, wherein the switching unit switches the communication speed to the higher communication speed allowable in the first controller on the basis of the information that is stored in the endoscope information memory and that is transmitted from the first controller to the second controller.

4. The endoscope apparatus according to claim 1, wherein the switching unit switches the communication speed to the higher communication speed allowable in the first controller on the basis of the information that is stored in the endoscope information memory and that is transmitted from the first controller to the second controller.

5. The endoscope apparatus according to claim 1, wherein, at startup, the communication speed setting unit sets the communication speed to a first communication speed that is at least lower than the higher communication speed and that is set in advance.

6. The endoscope apparatus according to claim 5, wherein the second controller transmits to the first controller a command to switch the communication speed to the higher communication speed and to set the higher communication speed with the first communication speed being set.

7. The endoscope apparatus according to claim 1, wherein the endoscope information memory stores as the information a value of the higher communication speed or communication speed information concerning the value of the higher communication speed.

8. The endoscope apparatus according to claim 1, wherein the communication unit includes a single communication line, in addition to a ground line.

9. The endoscope apparatus according to claim 1, wherein the communication unit includes, in addition to a ground line, a single communication line and a signal line.

10. The endoscope apparatus according to claim 9, wherein, after the transmission and reception of the data is terminated, the signal line is released from the operation of the communication unit.

11. The endoscope apparatus according to claim 9, wherein the signal line is used only for transmission of the information from the first controller to the second controller.

12. The endoscope apparatus according to claim 9, wherein, at startup, the first controller uses the signal line to transmit information concerning the higher communication speed allowable in the first controller.

13. The endoscope apparatus according to claim 12, wherein the first controller transmits the information concerning the higher communication speed at a voltage level corresponding to the higher communication speed.

14. The endoscope apparatus according to claim 9, wherein the first controller transmits, to the second controller through the signal line, a confirmation of the switching to the higher communication speed in response to the command.

15. An endoscope apparatus comprising:
an endoscope that includes an information storage section including an endoscope information memory in which information concerning the endoscope is stored and a first controller controlling readout of the information stored in the endoscope information memory;
a signal processing unit to which the endoscope is detachably connected and which includes a second controller issuing at least an instruction for a readout operation of the information to the information storage section;
a communication unit through which data is transmitted and received between the first controller and the second controller;
a communication speed setting unit setting the communication speed of the communication unit to a higher communication speed allowable in the first controller and the second controller; and
a switching unit switching the communication speed on the basis of a result produced in the communication speed setting unit,
wherein the switching unit switches the communication speed to the higher communication speed allowable in the first controller and the second controller on the basis of the information that is stored in the endoscope information memory and that is transmitted from the first controller to the second controller.

16. A communication method in an endoscope apparatus including an endoscope and a signal processing unit, the endoscope including an information storage section that includes an endoscope information memory in which information concerning the endoscope is stored and a first controller controlling readout of the information stored in the endoscope information memory, the signal processing unit to which the endoscope is detachably connected including a second controller issuing at least an instruction for a readout operation of the information to the information storage section, data being transmitted and received between the first controller and the second controller through a communication unit, the communication method comprising the steps of:

setting the communication speed of the communication unit to a higher communication speed allowable in the first controller; and     switching the communication speed on the basis of a result in the step of setting the communication speed, wherein the second controller transmits to the first controller a command to switch the communication speed to the higher communication speed and to set the higher communication speed on the basis of information concerning the higher communication speed allowable in the first controller, the information being stored in the endoscope information memory.

17. The communication method according to claim 16, wherein in the switching step the communication speed is switched on the basis of the information that is stored in the endoscope information memory and that concerns the higher communication speed.

* * * * *